United States Patent
Hu et al.

(10) Patent No.: US 11,733,219 B2
(45) Date of Patent: Aug. 22, 2023

(54) DETECTION REAGENT, DETECTION DEVICE, AND METHOD FOR DETECTING PRIMARY AMIDE COMPOUND

(71) Applicant: INDUSTRIAL TECHNOLOGY RESEARCH INSTITUTE, Hsinchu (TW)

(72) Inventors: Jie-Bi Hu, Zhubei (TW); Chin-Ping Huang, Hsinchu (TW); Meng-Tzu Lai, Taichung (TW); Hsiao-Mei Wu, Toufen (TW); Pei-Hua Yeh, Hsinchu (TW); Tzu-Chia Lai, New Taipei (TW); Jhih-Yun Lin, Tainan (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 173 days.

(21) Appl. No.: 17/206,443

(22) Filed: Mar. 19, 2021

(65) Prior Publication Data
US 2021/0293765 A1   Sep. 23, 2021

Related U.S. Application Data

(60) Provisional application No. 62/991,714, filed on Mar. 19, 2020.

(51) Int. Cl.
*C01G 55/00* (2006.01)
*G01N 30/88* (2006.01)
(Continued)

(52) U.S. Cl.
CPC ......... *G01N 30/88* (2013.01); *G01N 21/3103* (2013.01); *G01N 23/22* (2013.01);
(Continued)

(58) Field of Classification Search
CPC .................................................. C01G 55/00
See application file for complete search history.

(56) References Cited

U.S. PATENT DOCUMENTS

| | | | | |
|---|---|---|---|---|
| 2,891,957 A | * | 6/1959 | Allen | C07D 311/82 564/324 |
| 3,318,901 A | * | 5/1967 | Yonan | C07D 335/20 504/156 |
| 10,253,285 B2 | | 4/2019 | Fang et al. | |

FOREIGN PATENT DOCUMENTS

| CN | 102928530 A | 2/2013 |
|---|---|---|
| CN | 103760266 A | 4/2014 |

(Continued)

OTHER PUBLICATIONS

Clark et al., "Determination of urea using high-performance liquid chromatography with fluorescence detection after automated derivatisation with xanthydrol", Journal of Chromatography A, 2007, vol. 1161, pp. 207-213.

(Continued)

*Primary Examiner* — Jamel E Williams
*Assistant Examiner* — Alex T Devito
(74) *Attorney, Agent, or Firm* — Birch, Stewart, Kolasch & Birch, LLP

(57) ABSTRACT

Detection reagent is formed by reacting a catalyst and xanthydrol. The catalyst includes an active component loaded on a support, wherein the active component includes Pt, Ru, Rh, or a combination thereof, and the support includes carbon material, silica, alumina, or calcium carbonate. The detection reagent can be used to detect the primary amide compound.

15 Claims, 5 Drawing Sheets

(51) Int. Cl.
  *G01N 23/22* (2018.01)
  *G01N 21/31* (2006.01)
  *G01N 30/72* (2006.01)
  *G01N 30/02* (2006.01)

(52) U.S. Cl.
  CPC ............. *G01N 30/72* (2013.01); *C01G 55/00* (2013.01); *G01N 2030/027* (2013.01); *G01N 2030/884* (2013.01)

(56) References Cited

FOREIGN PATENT DOCUMENTS

| CN | 103954722 A | 7/2014 | | |
|---|---|---|---|---|
| CN | 106885905 A | 6/2017 | | |
| CN | 107703124 A | 2/2018 | | |
| CN | 109406424 A | 3/2019 | | |
| JP | H0610147 | * | 2/1994 | |
| JP | 2018-179545 A | | 11/2018 | |
| TW | 201842333 A | | 12/2018 | |
| TW | 201934998 A | | 9/2019 | |
| WO | WO-0110550 A1 | * | 2/2001 | ............ B01J 21/063 |

OTHER PUBLICATIONS

Zhang et al., "Simultaneous Determination of Ethyl Carbamate and Urea in Alcoholic Beverages by High-Performance Liquid Chromatography Coupled with Fluorescence Detection", Journal of Agricultural and Food Chemistry, 2014, vol. 62, pp. 2797-2802.

Taiwanese Office Action and Search Report for Taiwanese Application No. 110109939, dated Jan. 5, 2022.

Japanese Office Action for Japanese Application No. 2021-045858, dated Apr. 26, 2022, with English translation.

* cited by examiner

DETECTION REAGENT, DETECTION DEVICE, AND METHOD FOR DETECTING PRIMARY AMIDE COMPOUND

CROSS REFERENCE TO RELATED APPLICATION

This application claims the benefit of U.S. Provisional Application No. 62/991,714, filed on Mar. 19, 2020, the entirety of which is incorporated by reference herein.

TECHNICAL FIELD

The present disclosure is related to a detection reagent, and in particular it is related to a detection device and method for detecting a primary amide compound using a detection reagent.

BACKGROUND

Due to water shortage issues and industrial water demands, all countries in the world are actively involved in the development of reclaimed water and are gradually introducing this as industrial water to reduce the impact on people's livelihood. Taking Taiwan as an example, more than 40,000 tons of reclaimed water is used per day in the Southern Taiwan Science Park in 2021 for its investment scale expansion year by year, and also in response to the increase in industrial water demand, the insufficiency of local reservoir storage capacity, and the prevention of pro-duction-process stoppages and lower production capacities that can be caused by water shortages. Taiwan's high-tech reclaimed water plants comply with the actual industrial water demand specifications. Reclaimed water must meet 21 test specifications before it can be used. Among them, "urea" is a neutral small molecule (molecular weight is only 60), which makes it impossible to remove using current membrane technology. Urea is the most difficult item to detect and remove in water quality testing items. The specification of reclaimed water for urea is defined as 5 ppb. If the urea concentration in the water exceeds 5 ppb, the photolithography process using immersion lithography technology will produce a T-topping effect, which will affect the product line width and cause problems with semiconductor production. Therefore, the development of a water-urea detection system is of great importance to the development of semiconductor upstream and downstream industrial technology, such as reclaimed water plants at the water supply end, semiconductor-grade specialty chemicals using pure water, ultrapure water system vendors and supply chains, etc.

Therefore, there is an urgent need for new methods to detect urea in reclaimed water, process recycled water, pure water, and wastewater.

SUMMARY

One embodiment of the present disclosure provides a detection reagent which is formed by reacting a catalyst and xanthydrol, wherein the catalyst comprises an active component loaded on a support, and wherein the active component comprises Pt, Ru, Rh, or a combination thereof.

One embodiment of the present disclosure provides a method for detecting a primary amide compound, comprising: providing a sample to a detection reagent, so that the primary amide compound in the sample reacts with the detection reagent to form a product; and separating the product and detecting the properties of the product to confirm the concentration of the primary amide compound in the sample, wherein the detection reagent is formed by reacting a catalyst and xanthydrol, wherein the catalyst comprises an active component loaded on a support, and wherein the active component comprises Pt, Ru, Rh, or a combination thereof.

One embodiment of the present disclosure provides a detection device, comprising: a sample source; a mixing device, connected to the sample source to receive a sample, and the mixing device contains a detection reagent to react with the primary amide compound in the sample to form a product; a separation device, connected to the mixing device to separate the product; and an analysis device, connected to the separation device to detect the properties of the product and confirm the concentration of the primary amide compound in the sample, wherein the detection reagent is formed by reacting a catalyst and xanthydrol, wherein the catalyst comprises an active component loaded on a support, and wherein the active component comprises Pt, Ru, Rh, or a combination thereof.

DETAILED DESCRIPTION

Figure 1:
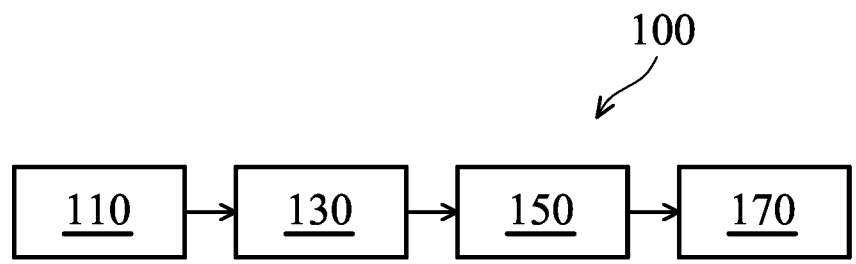
FIG. 1 is a schematic diagram of a detection device in one embodiment.

In the following detailed description, for purposes of explanation, numerous specific details are set forth in order to provide a thorough understanding of the disclosed embodiments. It will be apparent, however, that one or more embodiments may be practiced without these specific details.

One embodiment of the present disclosure provides a detection reagent is formed by reacting a catalyst and xanthydrol. In general, the usage amount of the xanthydrol is much larger than the catalyst. For example, xanthydrol can be dissolved in a solvent to form a solution, then the solution is mixed with the catalyst, and the catalyst is reacted with xanthydrol to form a detection reagent. The foregoing solvent includes, for example, methanol, ethanol, isopropanol, other solvents that do not react with the catalyst, or a combination thereof, but it is not limited thereto. The structure of xanthydrol is The foregoing catalyst includes an active component loaded on a support. For example, the active component includes Pt, Ru, Rh, or a combination thereof, but it is not limited thereto. The support includes carbon material, silica, alumina, or calcium carbonate, but it is not limited thereto. In some embodiments, carbon material can be activated carbon made from different raw materials, including coconut shell, Vulcan XC-72, or AC01, but it is not limited thereto. In some embodiments, the active component can be Pt, and the support can be carbon material, such as activated carbon. In some embodiments, particle size d50 of the support is 3 μm to 3 mm, for example, 15 μm to 80 μm, 18 μm, 40 μm, or 70 μm, but it is not limited thereto. The specific surface area of the support is 7 $m^2$/g to 1500 $m^2$/g, for example, 100 $m^2$/g to 1200 $m^2$/g, 110 $m^2$/g, 400 $m^2$/g, or 900 $m^2$/g, but it is not limited thereto. If the specific surface area of the support is too small, the activity of the catalyst will decrease, that is, the effect of reacting with xanthydrol to form a detection reagent is not good. If the specific surface area of the support is too large, the strength of the support will decrease and it will easily to break down. In some embodiments, the weight ratio of the active component to the support is from 0.5:99.5 to 80:20, for example, 0.5:99.5, 40:60, 70.9:29.1, or 76.6:23.4, but it is not limited thereto. If the ratio of the active component is too low, the catalyst activity is insufficient. If the ratio of the active component is too high, the catalytic effect will be reduced. It is noted that, strong acids such as HCl, $C_2HF_3O_2$, $HNO_3$, $H_2SO_4$, or other strong acids are often used as catalysts for the reaction of urea with xanthydrol, the reaction is as follows:

The detection reagent formed in the present disclosure, and the reaction of the detection reagent and urea is as follows:

It is understandable that in addition to urea, the foregoing detection reagent can react with other primary amide compounds as follows:

wherein R refers to a hydrogen atom or an organic group. Compared with a reaction using a strong acid as a catalyst, the product formed by first using a catalyst reacting with xanthydrol to form a detection reagent and then the detection reagent reacting with the primary amide compound is more stable in one embodiment of the present disclosure. The reaction product using a strong acid as a catalyst produces a large amount of by-products after a period of time (e.g., 12 hours), and the product after the reaction of the detection reagent and the primary amide compound can be stored stably for a long time (e.g., 7 days). On the other hand, the reaction time of the detection reagent and urea to form a product (less than 1 minute) is much shorter than the reaction time of urea and xanthydrol under a strong acid catalyst (about 30 minutes).

One embodiment of the present disclosure provides a method for detecting a primary amide compound, comprising: providing a sample to a detection reagent, so that the primary amide compound in the sample reacts with the detection reagent to form a product. In one embodiment, the primary amide compound can be urea. In other embodiments, the primary amide compound includes urea, glutamine, asparagine, or a combination thereof, but it is not limited thereto. In some embodiments, the sample contains water such as reclaimed water, process recycled water, pure water or wastewater, but it is not limited thereto. When the primary amide compound is urea, the Limit of Detection (LOD) of urea in the sample can reach 3 ppb or lower. Since the current urea specification of reclaimed water in Taiwan is 5 ppb, it is sufficient to confirm whether the urea in the reclaimed water meets the water supply specification according to an embodiment of the disclosure.

In some embodiments, the detection reagent can be packed in the column, and the sample can elute the detection reagent in the column, so that the primary amide compound (such as urea) in the sample reacts with the detection reagent to form a product. Since the low polarity of detection reagent, xanthydrol needs to be added to the polar sample (such as pure water) to make the polarity of the sample approximate to the polarity of the detection reagent, and to avoid the large polarity difference between them and unable to elute smoothly. If the sample is of low polarity, it can be directly added to the column to react with the low polarity detection reagent.

If the foregoing column is used for the reaction, the time from the sample entering the column to leaving the column can be adjusted by the size of the column, the length of the column, and the sample flow rate, such as less than 1 minute. The above time is sufficient for the urea in the sample to react with the detection reagent to form a product. If the time is too short, such as the elution speed is too fast, the proportion of the product formed by the urea reaction is too low to analyze its properties. On the other hand, if the time is too long, such as the elution speed is too slow, the analysis time will be extended and the detection efficiency will be reduced.

Next, the product is separated and the properties of the product is tested to confirm the concentration of the primary amide compound in the sample. For example, the liquid flowing out from the column mainly contains water (or other solvents), xanthydrol and its derivatives, and the above-mentioned products. Since the proportion of xanthydrol is much greater than the product, the liquid flowing out from the column needs to be separated before measuring its properties to avoid signal coverage or interference with the signal of the product by xanthydrol. In some embodiments, the liquid chromatography is used in the separating step of the product, and the analyzing step of the properties of the product includes analyzing the fluorescence intensity, molecular weight, or ultraviolet absorption intensity of the product. In some embodiments, the above measurement can last for 150 hours without changing the detection reagent in the column, so the detection process can be simplified.

In some embodiments, the sample can be directly mixed and reacted with the detection reagent to form a product without filling the detection reagent into the column. If this method is adopted, the solids such as catalysts must be removed by filtration after the reaction, and then the product will be separated from the mixture (including water or other solvents, xanthydrol and its derivatives, and the product) after the reaction, and the properties of the product will be analyzed. Since the product after the reaction can exist stably for a long time, it can be stored for a period of time before separation and analysis, and a part of it can be kept for future reference.

One embodiment of the present disclosure provides a detection device 100, as shown in FIG. 1. The detection device 100 may include a sample source 110 and a mixing device 130. The mixing device 130 is connected to the sample source 110 to receive the sample, and the mixing device 130 contains the foregoing detection reagent to react with the primary amide compound in the sample to form a product. In some embodiments, the mixing device 130 may be a column to fill the detection reagent. Since the low polarity of detection reagent in general, xanthydrol may be added to the sample in the sample source 110, to make the polarity of the sample approximate to the polarity of the detection reagent, and to facilitate subsequent reaction to form a product.

The detection device 100 may also include a separation device 150 connected to the mixing device 130 to separate the product. In some embodiments, the separation device 130 may be a liquid chromatography column. The detection device 100 may also include an analysis device 170 connected to the separation device 150 to detect the properties of the product (e.g. fluorescence intensity, molecular weight, or ultraviolet absorption intensity) and confirm the concentration of the primary amide compound in the sample. For example, the analysis device 170 may be a fluorescence spectrometer, a mass spectrometer, or a visible light-ultraviolet absorption spectrometer, etc.

In order to make the above content and other objects, features, and advantages of the present disclosure more comprehensible, the following describes the preferred embodiments with the accompanying drawings in detail, as follows:

EXAMPLES

Example 1

Pt, Ru, and Rh were loaded on activated carbon respectively to form Pt/C (loading amount is 5%, specific surface area is 900 m²/g, Strem Chemicals, Catalog number 78-1611), Ru/C (loading amount is 5%, Strem Chemicals, Catalog number 44-4050), and Rh/C (loading amount is 5%, Sigma Aldrich, Catalog number 206164) catalysts. After filling the foregoing catalysts into the column, the solution of xanthydrol and alcohols was added to the column, to make the catalyst react with xanthydrol for 15 minutes to obtain the detection reagent.

The prepared sample (the solution containing 5 ppb of urea and 0.4% (w/v) xanthydrol) was added into the column at a flow rate of 1 mL/min to make the urea in the sample reacting with the detection reagent, and to form the following products:

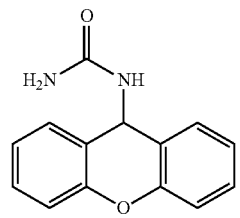 [SMILES: NC(=O)NC1c2ccccc2Oc2ccccc21]

Figure 2:
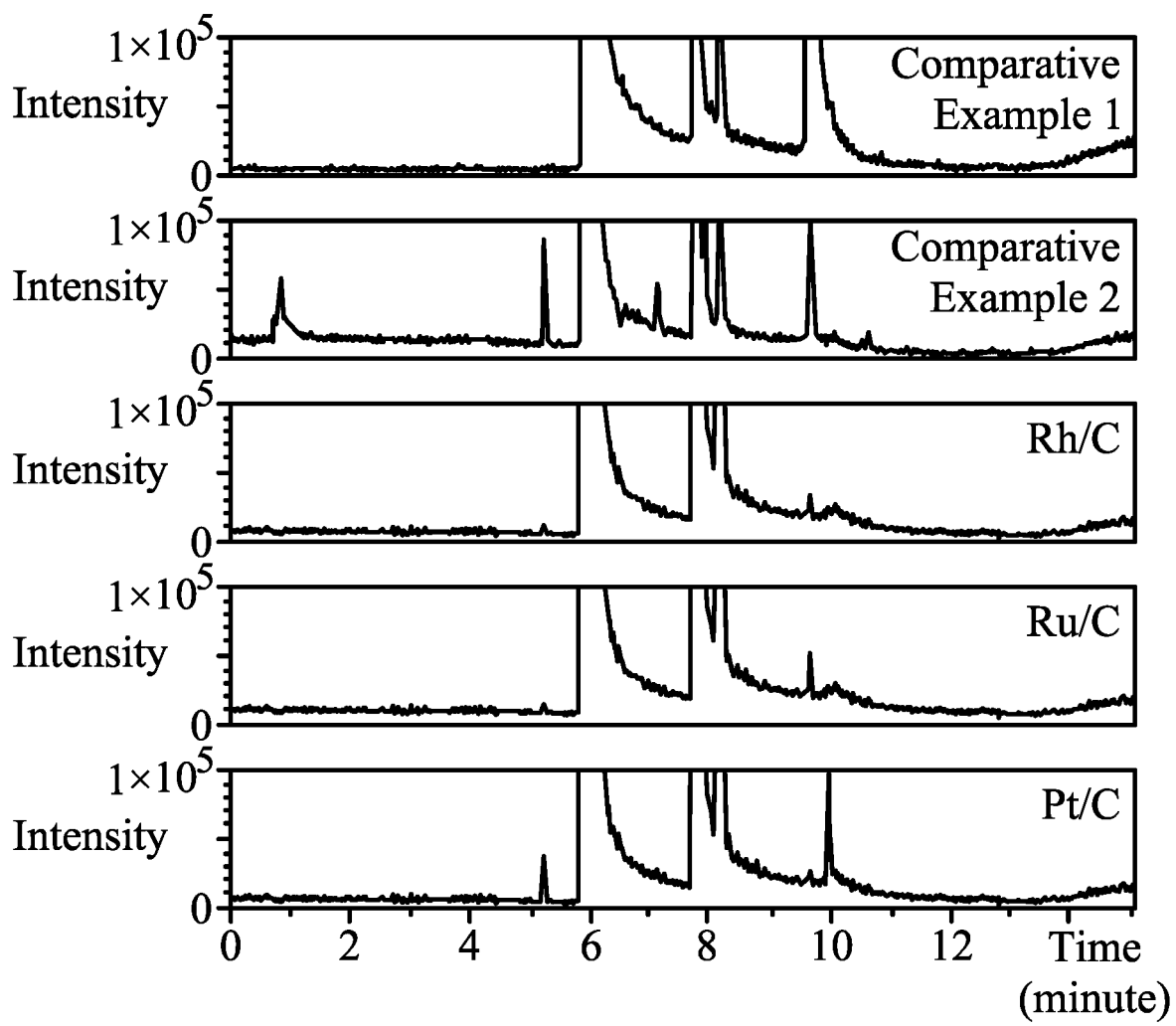
FIG. 2 is a mass spectrum measured after a sample containing urea is reacted with different detection reagents and separated by a liquid chromatography column in one embodiment.

The time from the sample entering the column to leaving the column is less than 1 minute, which can be regarded as the time required for the reaction between urea and the detection reagent. Then, the liquid (mainly containing water, xanthydrol and its derivatives, and the foregoing product) flowing out of the column was passed into the liquid chromatography column, and the product signal is measured by a fluorescence spectrometer. The retention time of the product signal is about 5 minutes. As shown in FIG. 2, Pt/C, Ru/C, and Rh/C all have product signals, and the product signal of Pt/C is particularly obvious.

Figure 3:
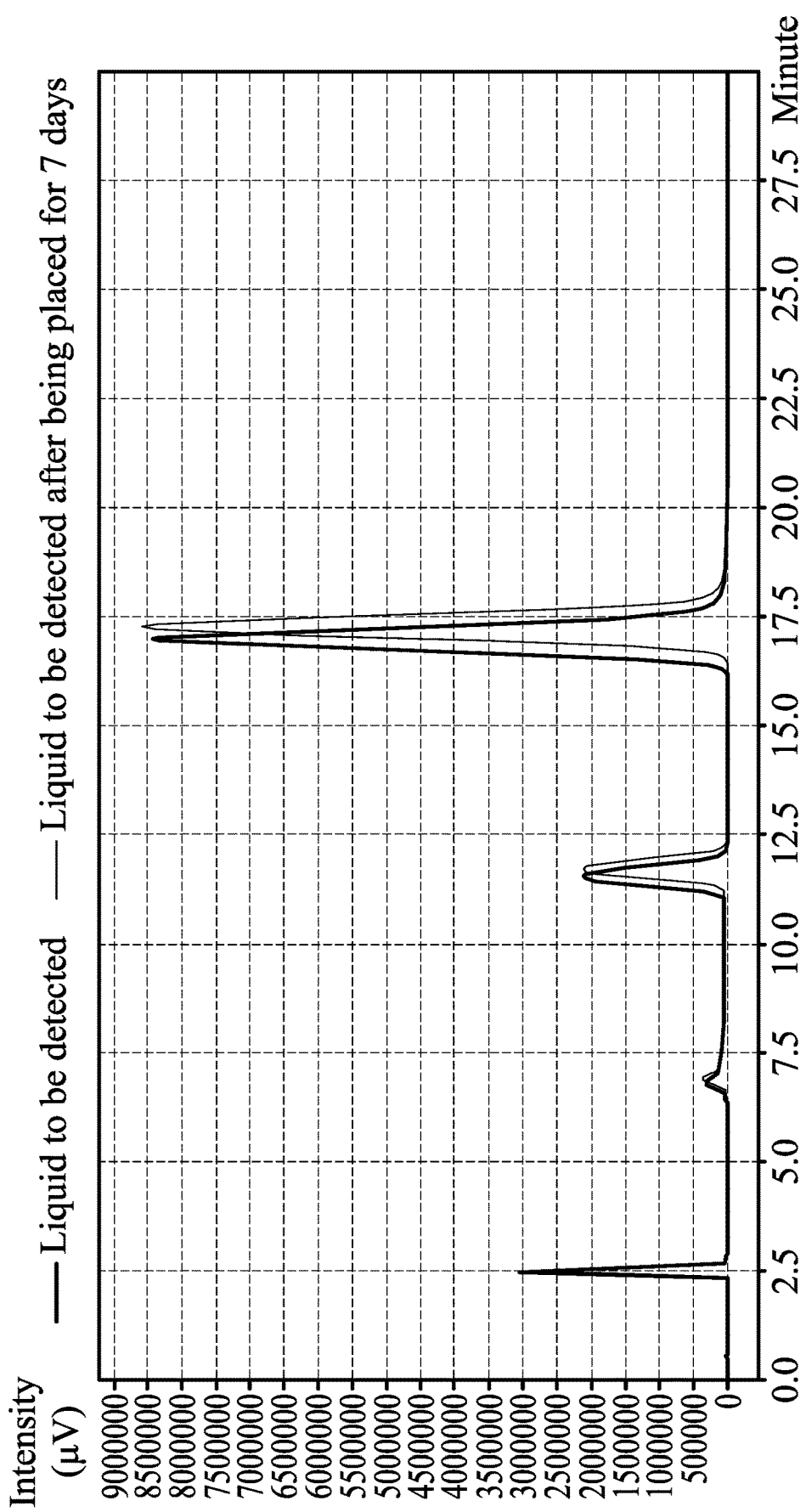
FIG. 3 is a fluorescence spectrum measured before and after the urea-containing sample reacts with the detection reagent and placed for 7 days, and is separated by the liquid chromatography column in one embodiment.

The liquid flowing out from the Pt/C column was placed for 7 days, then passed into the liquid chromatography column, and the product signal was measured with a fluorescence spectrometer. The result of the above measurement was shown in FIG. 3, and it can be seen that the product formed after the reaction with the detection reagent can be stored stably for a long time without a large amount of by-products. In this way, if the schedule of liquid chromatography column and/or the fluorescence spectrometer is fully loaded, the product can still be stored for a period of time without immediate measurement. On the other hand, a portion of the liquid flowing out of the column can be stored for future reference.

Comparative Example 1

The prepared sample (the solution containing 5 ppb of urea and 0.4% (w/v) xanthydrol) was placed for 30 minutes, then passed into the liquid chromatography column, and the product signal was measured with a mass spectrometer. There was no product signal at the retention time of about 5 minutes, as shown in FIG. 2. It can be seen from the above that in the absence of a catalyst, urea was hardly reacted with xanthydrol.

Comparative Example 2

The prepared sample (the solution containing 5 ppb of urea and 0.4% (w/v) xanthydrol) was added with 1.5M HCl, then passed into the liquid chromatography column, and the product signal was measured with a mass spectrometer. The intensity of product signal at the retention time of about 5 minutes is low.

The prepared sample (the solution containing 5 ppb of urea and 0.4% (w/v) xanthydrol) was added with 1.5M HCl and reacted for 30 minutes, then passed into the liquid chromatography column, and the product signal was measured with a mass spectrometer. The intensity of product signal at the retention time of about 5 minutes is high, as shown in FIG. 2. It can be seen from the above that the reaction time required for the reaction of urea and xanthydrol to form a product under the HCl catalyst is up to 30 minutes, which is much longer than the time required for the reaction of the detection reagent and urea in one embodiment of the present disclosure.

Figure 4:
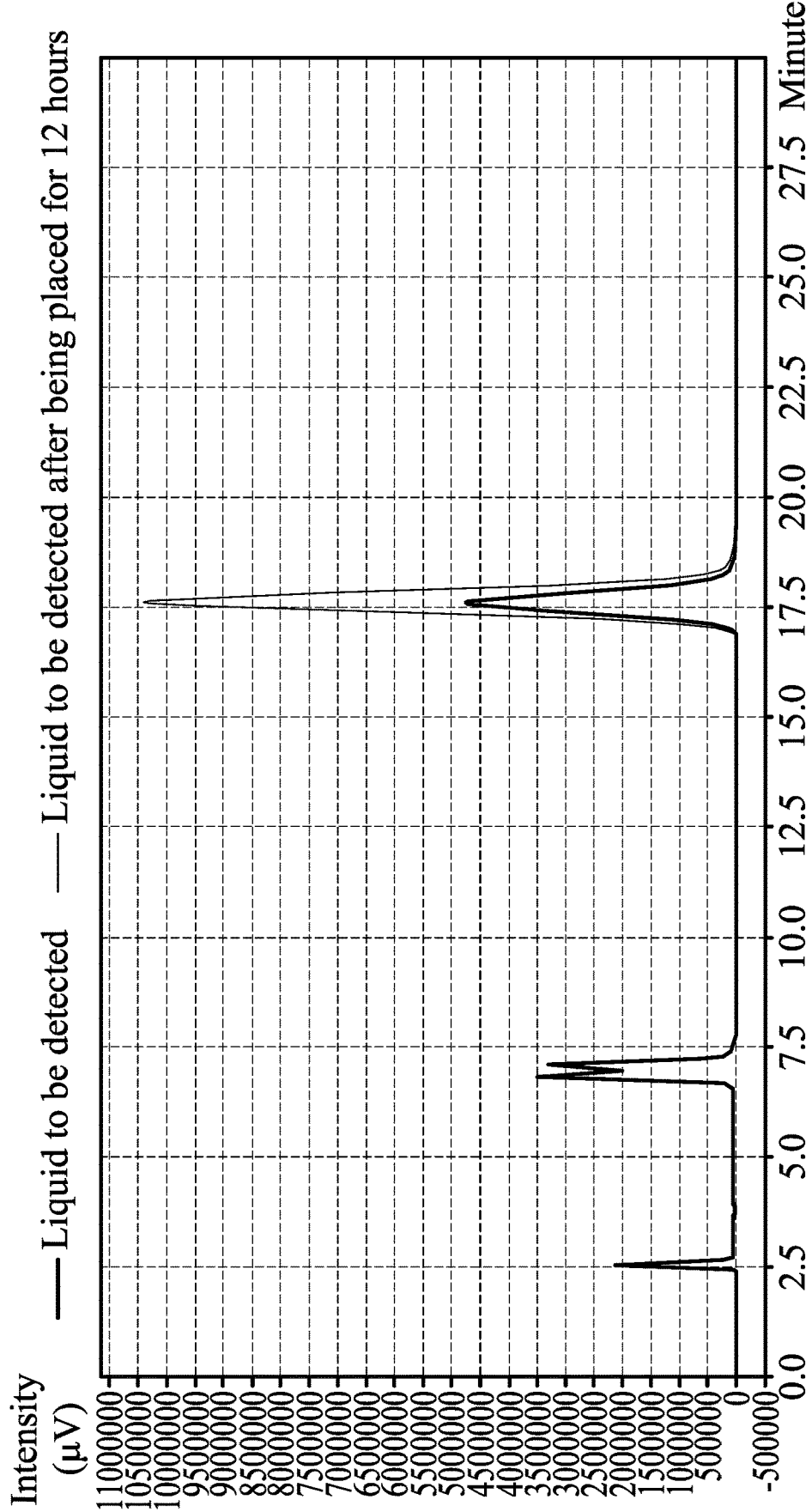
FIG. 4 is a fluorescence spectrum measured before and after the urea-containing sample reacts with xanthydrol under HCl catalyst and placed for 12 hours, and is separated by the liquid chromatography column in one embodiment.

The sample was reacted with HCl for 30 minutes to form the product, and the product was passed into the liquid chromatography column after placed for 12 hours, and the product signal was measured with a fluorescence spectrometer. The results of the above measurement are shown in FIG. 4. It can be seen that after urea reacted with xanthydrol under the HCl catalyst, a large amount of by-products (retention time is about 17.5 minutes) were produced after a short time. In this way, the above product must be measured immediately after the reaction and cannot be stored for a long time.

Example 2

Figure 5:
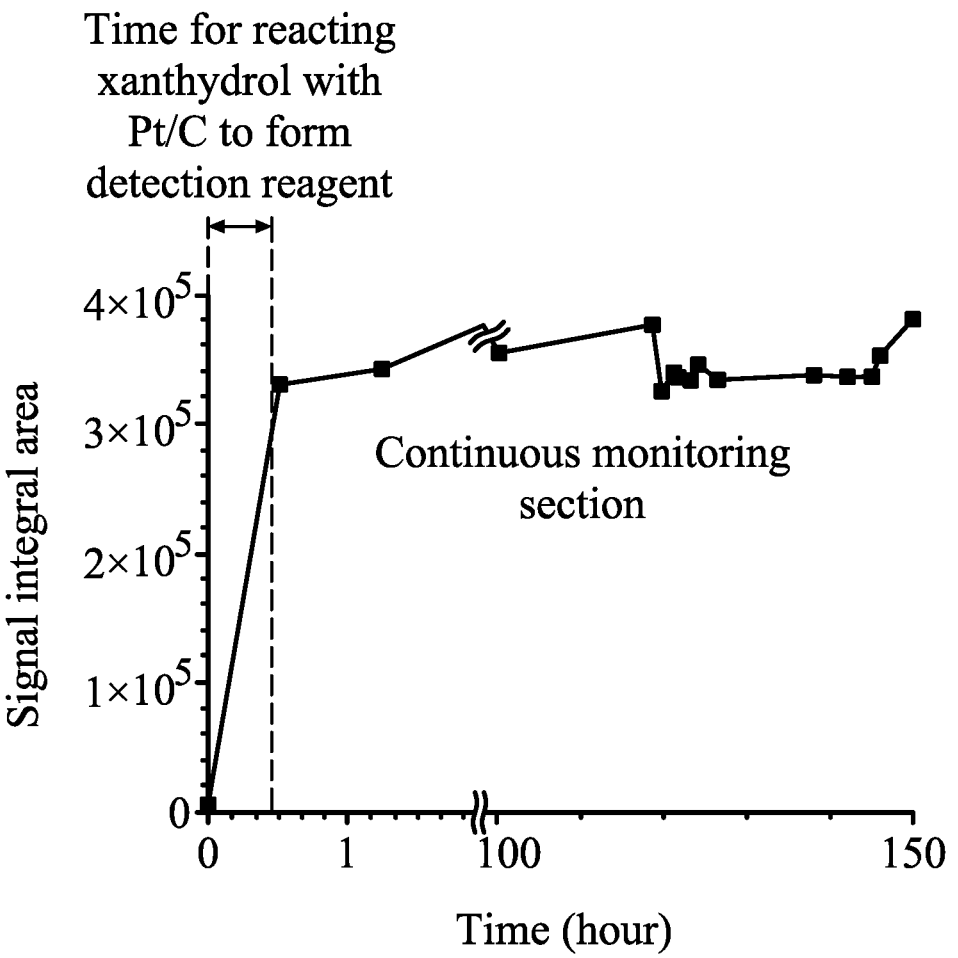
FIG. 5 shows the signal integrated area measured after the urea-containing sample is continuously passed through the detection reagent for 150 hours and then separated by the liquid chromatography column in one embodiment.

Similar to the detection reagent (using Pt/C catalyst) and the sample in Example 1, except that the sample is continuously passed through the column for 150 hours. The liquid flowing out from the column (mainly containing water, xanthydrol and its derivatives, and the foregoing product) was passed into the liquid chromatography column, and the signal integral value was measured for about 2 minutes with a fluorescence spectrometer, as shown in FIG. 5. It can be known from FIG. 5 that the continuous measurement time of the above system can be as high as 150 hours.

Example 3

Figure 6:
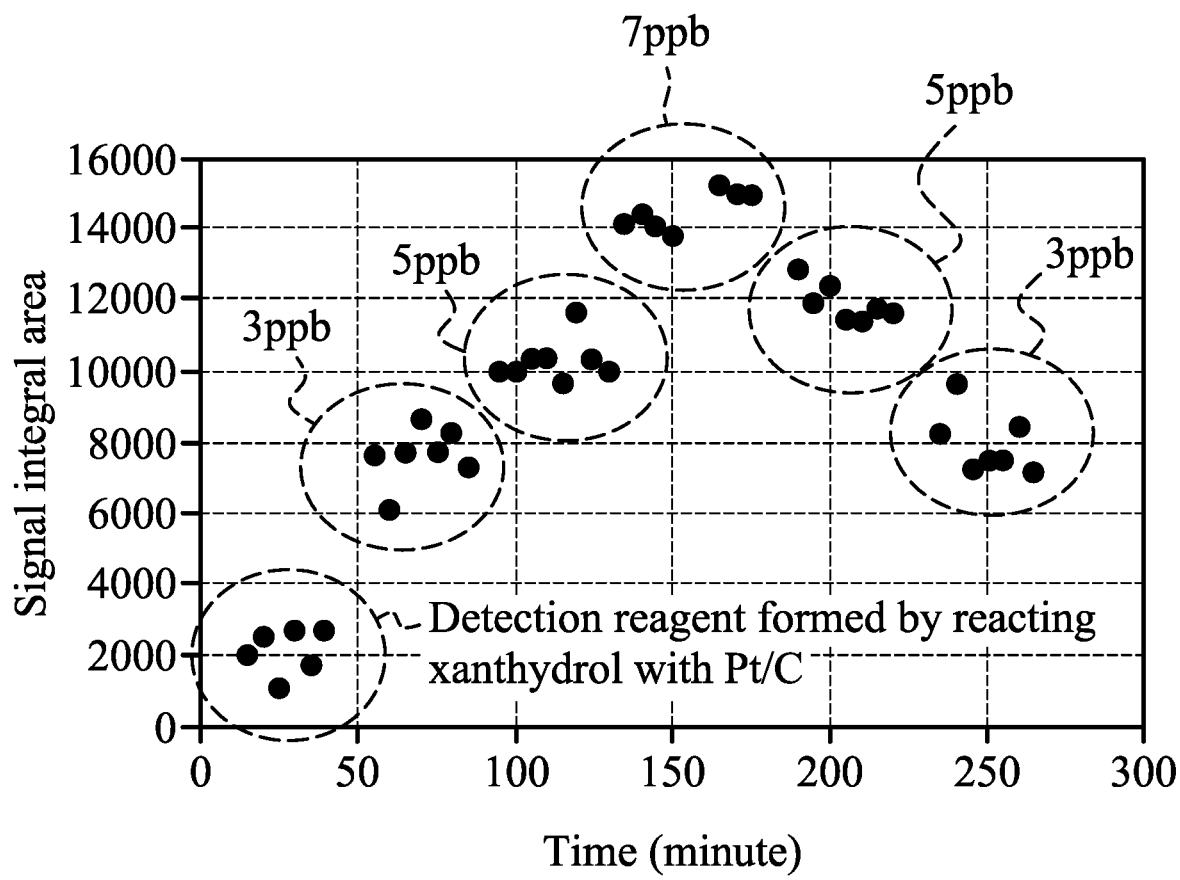
FIG. 6 shows the signal integrated area measured after the different concentrations of urea-containing samples passed through the detection reagents and then separated by the liquid chromatography column in one embodiment.

Similar to the detection reagent (using Pt/C catalyst) and the sample in Example 1, except that the sample solutions (all containing 0.4% (w/v) of xanthydrol) containing 3 ppb, 5 ppb, 7 ppb, 5 ppb, and 3 ppb of urea were sequentially passed through the column at different time. The liquid flowing out from the column (mainly containing water, xanthydrol and its derivatives, and the foregoing product) was passed into the liquid chromatography column, and the signal integral value was measured for about 2 minutes with a fluorescence spectrometer, as shown in FIG. 6. It can be known from FIG. 6 that the above detection system can distinguish the difference of urea concentration from 0 ppb to 7 ppb in the sample.

Example 4

Pt was loaded on activated carbon (specific surface area is 900 m2/g, Strem Chemicals, Catalog number 78-1611) to form Pt/C (loading amount is 5%). 6 mg of Pt/C, 3 mL of xanthydrol and 3 mL of the prepared sample (containing 33 ppm of urea, glutamine, asparagine solution and 0.4% (w/v) of xanthydrol) was reacted for 30 minutes, so that the primary amide compound in the sample was reacted with the detection reagent to form the product as follows:

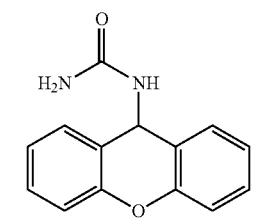 [SMILES: NC(=O)NC1c2ccccc2Oc2ccccc21]

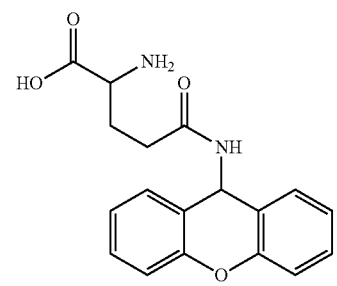 [SMILES: NC(CCC(=O)NC1c2ccccc2Oc2ccccc21)C(=O)O]

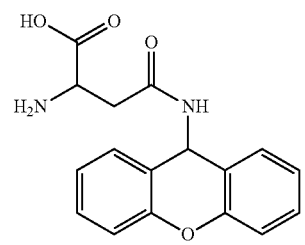 [SMILES: NC(CC(=O)NC1c2ccccc2Oc2ccccc21)C(=O)O]

The solids such as catalysts in the mixture were removed by filtration or centrifugation after the reaction, then the liquid (mainly containing water, xanthydrol and its derivatives, and the foregoing product) was passed into the liquid chromatography column, and the product signal was measured with a fluorescence spectrometer. The retention time of the product signals in order were about 1.4 minutes for asparagine, about 1.6 minutes for glutamine, and about 2.0 minutes for urea. It can be seen from the above that the detection reagent can be used to detect not only urea but also other primary amide compounds.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A detection reagent is formed by reacting a catalyst and xanthydrol, wherein the catalyst comprises an active component loaded on a support, and wherein the active component comprises Pt, Ru, Rh, or a combination thereof.

2. The detection reagent as claimed in claim 1, wherein the support comprises carbon material, silica, alumina, or calcium carbonate.

3. The detection reagent as claimed in claim 1, wherein a particle size d50 of the support is 3 µm to 3 mm, and
wherein the specific surface area of the support is 7 $m^2/g$ to 1500 $m^2/g$.

4. The detection reagent as claimed in claim 1, wherein the weight ratio of the active component to the support is from 0.5:99.5 to 80:20.

5. The detection reagent as claimed in claim 1, wherein the detection reagent does not contain a strong acid.

6. A method for detecting a primary amide compound, comprising:
providing a sample to a detection reagent, so that the primary amide compound in the sample reacts with the detection reagent to form a product; and
separating the product and detecting the properties of the product to confirm a concentration of the primary amide compound in the sample,
wherein the detection reagent is formed by reacting a catalyst and xanthydrol, wherein the catalyst comprises an active component loaded on a support, and wherein the active component comprises Pt, Ru, Rh, or a combination thereof.

7. The method as claimed in claim 6, wherein the support comprises carbon material, silica, alumina, or calcium carbonate.

8. The method as claimed in claim 6, wherein the detection reagent is packed in a column, and the sample further comprises xanthydrol, so that the polarity of the sample is similar to the polarity of the detection reagent.

9. The method as claimed in claim 6, wherein the step of separating the product uses liquid chromatography, and the step of detecting the properties of the product comprises detecting the fluorescence signal, molecular weight, or ultraviolet absorption signal of the product.

10. The method as claimed in claim 6, wherein the primary amide compound comprises urea, glutamine, asparagine, or a combination thereof.

11. A detection device, comprising:
a sample source;
a mixing device, connected to the sample source to receive a sample, and the mixing device contains a detection reagent to react with the primary amide compound in the sample to form a product;
a separation device, connected to the mixing device to separate the product; and
an analysis device, connected to the separation device to detect the properties of the product and confirm the concentration of the primary amide compound in the sample,
wherein the detection reagent is formed by reacting a catalyst and xanthydrol,
wherein the catalyst comprises an active component loaded on a support, and
wherein the active component comprises Pt, Ru, Rh, or a combination thereof.

12. The detection device as claimed in claim 11, wherein the support comprises carbon material, silica, alumina, or calcium carbonate.

13. The detection device as claimed in claim 11, wherein the mixing device is a column, and the sample further comprises xanthydrol, so that the polarity of the sample is similar to the polarity of the detection reagent.

14. The detection device as claimed in claim 11, wherein the separation device comprises liquid chromatography, and the analysis device comprises fluorescence spectrometry, mass spectrometry, or visible-ultraviolet absorption spectrometry.

15. The detection device as claimed in claim 11, wherein the primary amide compound comprises urea, glutamine, asparagine, or a combination thereof.

* * * * *